United States Patent [19]

Tsao

[11] Patent Number: 4,919,816

[45] Date of Patent: Apr. 24, 1990

[54] REMOVAL OF ACIDIC IMPURITIES IN PROCESSES FOR SOLVENT EXTRACTION OF AROMATICS FROM NONAROMATICS

[75] Inventor: Hsiang-Wei Tsao, West Chester, Pa.

[73] Assignee: Sun Refining and Marketing Company, Philadelphia, Pa.

[21] Appl. No.: 304,090

[22] Filed: Jan. 31, 1989

[51] Int. Cl.⁵ .......................... B01D 11/04; C02F 1/42
[52] U.S. Cl. ..................................... 210/638; 210/683
[58] Field of Search ................. 210/683, 638; 568/621

[56] References Cited

U.S. PATENT DOCUMENTS 2,878,182  3/1959  Bloch ................................. 568/621
4,518,396  5/1985  Rawson .............................. 568/621

Primary Examiner—Ivars Cintins
Attorney, Agent, or Firm—J. Edward Hess; Donald R. Johnson

[57] ABSTRACT

Corrosion of process equipment in a system for extraction of aromatic components from nonaromatic components by means of a selective solvent, for example tetraethylene glycol, is reduced by treating with anion exchange resin a stream composed mainly of water which has been used to wash residual solvent from the extracted aromatics.

4 Claims, 2 Drawing Sheets

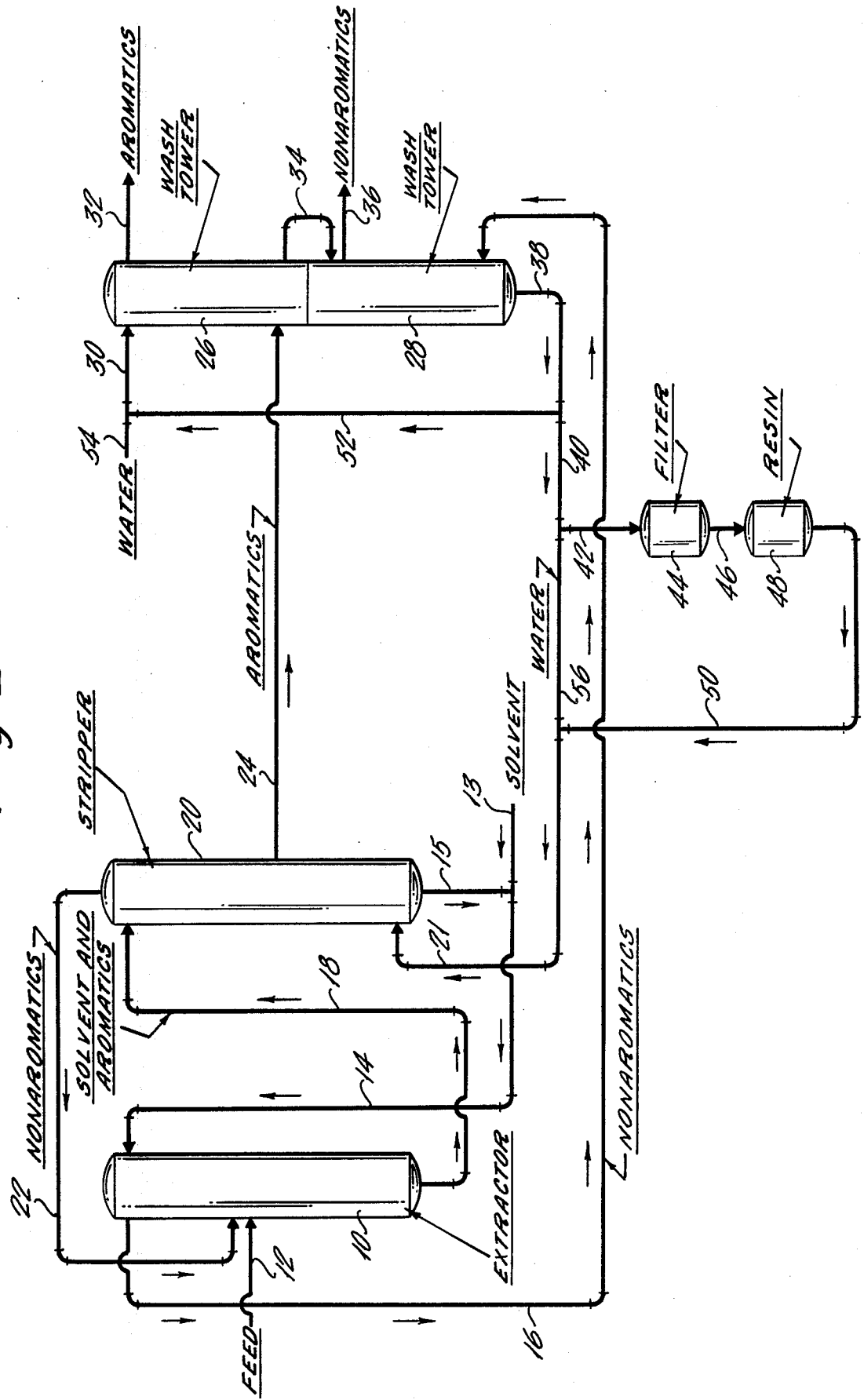

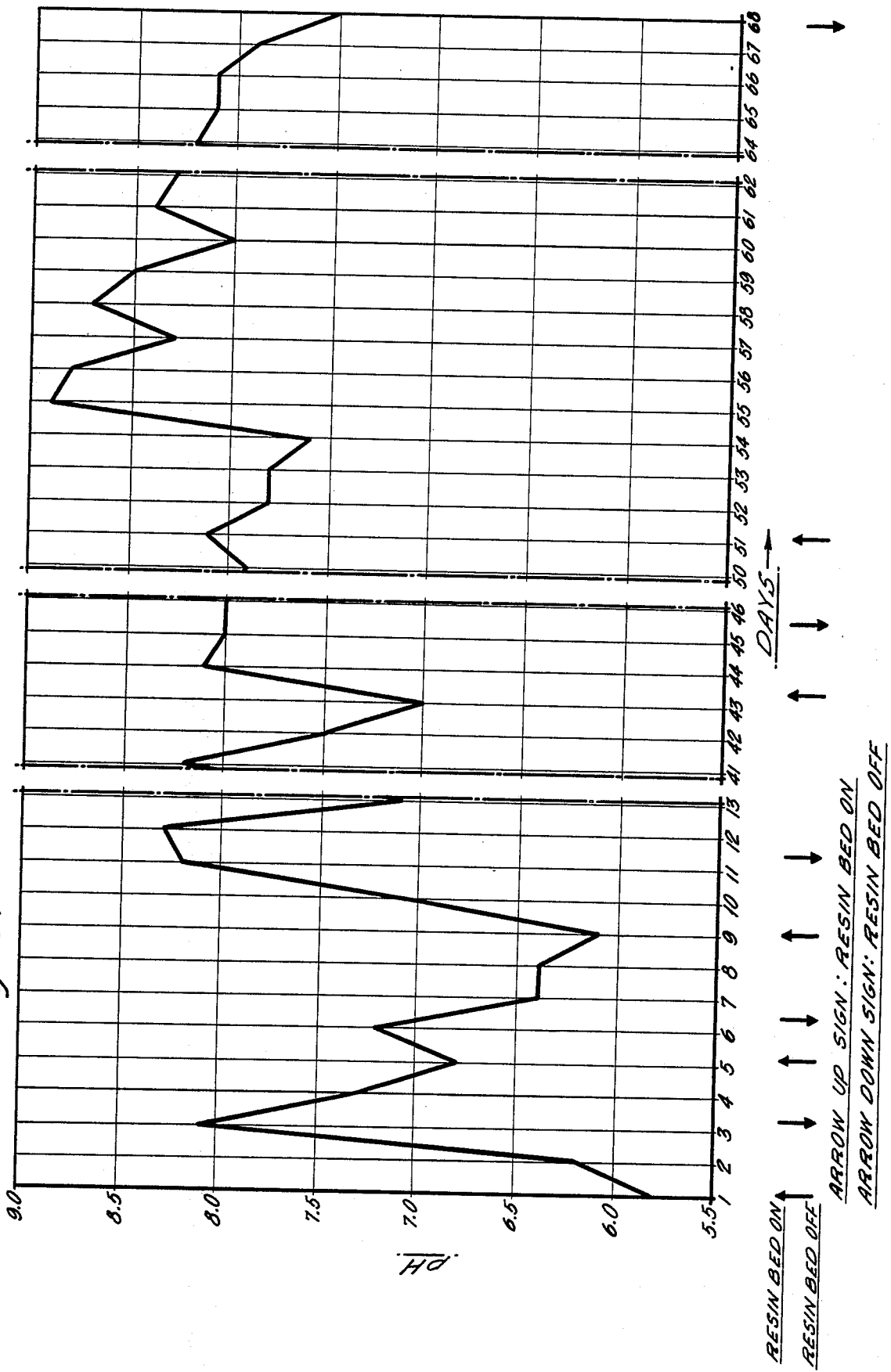

REMOVAL OF ACIDIC IMPURITIES IN PROCESSES FOR SOLVENT EXTRACTION OF AROMATICS FROM NONAROMATICS

BACKGROUND OF THE INVENTION

This invention relates to processes for extraction of aromatic compounds from nonaromatic compounds by means of selective solvents for aromatic compounds, and more particularly to a novel method of controlling corrosion in the solvent recovery systems of such processes.

In such processes, the principal products of the extraction step are a solvent phase containing principally solvent and extracted aromatic compounds and a raffinate phase containing principally unextracted nonaromatic compounds. The solvent phase is customarily distilled to separate a product containing principally solvent from a product, the extract, containing principally aromatic compounds. The solvent is recycled to the extraction step for reuse in the extraction process.

Frequently, in such process systems, acidic products are generated as a result of oxidation of the solvent. For example, in one system using triethylene glycol as the solvent, it has been found that the rate of formation of proton ($H^+$) in the solvent, at 150° C. in the presence of air is $1.921 \times 10^{-7}$ mole per liter per 33 hours. In the same period, the pH of the process water in the system dropped from 8.10 to 6.63. Acids generated by solvent decomposition have caused corrosion problems in of the process systems. The major contaminants in the solvent and in the water system have been found to be iron-containing particulates, apparently from corrosion of process equipment caused by the acidic contaminants.

DESCRIPTION OF THE PRIOR ART

A method previously used to control the system pH has been the addition of monoethanolamine (MEA) to neutralize the acids and form MEA salts. However, this leads to foaming problems because of the surfactant properties of the salts. To counteract such problems, antifoaming compounds may be added. However, as the concentrations of the salts, antifoaming conpounds and particulates build up in the system, the performance of the system may deteriorate.

Charcoal beds may also be used to remove acids and color contaminants from the solvent. However, there are problems in such use in that charcoal does not adjust pH effectively, in that charcoal may lose its capacity for removal of color contaminants within two to three weeks and in that air trapped in the charcoal pores may be introduced into the system during each loading step.

In prior U.S. Pat. No. 2,878,182, a process for eliminating acid buildup in a solvent system for extraction of aromatics from nonaromatics is disclosed, in which a solvent stream is treated with ion exchange resin Such operation has several disadvantages, however, since the temperature of the solvent stream may be higher than the maximum safe temperature for the resin, and it may therefore be necessary to cool the solvent stream before treating with the resin. Another disadvantage is that the amount of acid build-up in the solvent stream may be much less than that in the wash water system, and treatment of the solvent may therefore be relatively ineffective against acid build-up overall. Also, the solvent stream is typically a much higher volume stream than the wash water stream, thus requiring undesirably large amounts of resin. These disadvantages are overcome by the process according to the invention, wherein the wash water stream is treated with resin. The volumes to be treated in the process according to the invention are relatively small, the treated material is relatively high in its content of contaminants to be removed from the system, and the treated material is typically already at a temperature below the maximum safe temperature of the resin, so that cooling is unnecessary.

DESCRIPTION OF THE INVENTION

According to the present invention, the disadvantages of operation according to the prior art are overcome by using an anion exchange resin to treat a stream composed mainly of water which has been used to wash residual solvent from the extracted aromatics obtained in solvent extraction of aromatics from nonaromatics. Typically, the water will have also been used in stripping of hydrocarbons from solvent following the extraction step.

The anion exchange resins which can be used according to the invention include macroreticular and gel type resins with weakly functional groups, such as the tertiary amine functional group. In such resins the tertiary amine function is bonded to an organic polymer backbone directly, or through one or more carbon atoms, or through a combination of carbon and nitrogen bonds. The tertiary amine function, may, for example, be the N,N-dimethylamine group or the N,N-diethylamine group. Such groups may be bonded directly, or indirectly to a polystyrene polymer backbone, that may be cross-linked with divinylbenzene. Alternately, the tertiary amine group may be bonded directly, or indirectly to an acrylic acid or methacrylic acid polymer that may also be cross-linked with divinylbenzene, or to a phenolic polymer. Examples of such resins include the commercially available resins marketed by Rohm and Haas under the trademarks Amberlyst A-21, Amberlite IRA-68, Amberlite IR-45, Amberlite XE-236 and the resin marketed under the trademark Duolite S-761.

The anion exchange resins which can be used according to the invention also include the ion exchange resins with strongly basic functional groups, in which the quaternary ammonium function is bonded to an organic polymer backbone, either directly or through one or more carbon atoms. The quaternary ammonium function may, for example, be the trimethylammonium hydroxide base, or the trimethylammonium chloride or trimethylammonium bromide groups bonded to a polystyrene backbone, that may be cross-linked with divinylbenzene. Examples of such resins include the commercially available resins marketed by Rohm and Haas under the trademarks Amberlyst A-26, Amberlyst A-27, Amberlite IRA-904, Amberlite IRA-410, Amberlite IRA-400(OH), Amberlite IRA 458 and the resin marketed under the trademark Dowex 1X2-100.

The method according to the invention is carried out by contacting the process water with the particulate resin, typically by passing the water through a bed of the resin. More than one bed of resin may be employed if desired, in series and/or in parallel. The bed or beds may be preceded by a filter in order to remove particulate matter and avoid fouling of the resin therewith.

An entire process water stream within the system may be passed through the resin bed or beds. Alternatively, a drag stream may be withdrawn from the resin stream for passage through the resin bed or beds and return to the main stream. Alternatively, a stream may be contacted with resin part of the time and bypassed around the resin treatment part of the time.

The temperature and pressure of the contacting of the process water stream with the resin bed are typically those at which the stream exists under the conditions ordinarily prevailing in the process as practiced in the prior art. The temperature should not exceed any temperature limitations peculiar to the resin used. For example, the temperature is preferably below 100° C. if Amberlyst 21 resin is used, and below 60° C. if Amberlyst 27 is used. Flow rate of the feed stream through a resin bed may be readily selected by a person skilled in the art. Particularly good results are obtained with liquid hourly space velocity in the range from 8 to 25 volumes of feed per volume of resin bed per hour.

The resin bed is preferably periodically regenerated by suitable procedure, for example by backflushing with water and with dilute alkali. In a typical procedure, the bed is backflushed with three times the bed volume of water, followed by backflushing with twice the bed volume of 3% aqueous sodium hydroxide and another backflushing with three times the bed volume of water.

Solvents for use in extraction processes to which the invention is applicable include oxygen-containing compounds such as acyclic and cyclic alcohols, glycols, glycol ethers and glycol esters. Suitable glycols useful in admixture with water include ethylene, propylene and butylene glycols such as ethylene glycol, diethylene glycol, triethylene glycol, tetraethylene glycol, propylene glycol, tripropylene glycol, and butylene glycol.

Other suitable solvents include sulfolane, N-methyl pyrrolidone, butyrolactone, phenol, dimethyl formamide, furfural, dimethyl sulfoxide, resorcinol, diethanolamine, butylcarbitol and other known selective solvents for aromatics.

Solvents having specific gravity above 1.1 are preferred, for ease of use in conventional extraction equipment. Conditions in the extraction such as temperature, solvent to feed ratio, and the type of equipment are those which are conventionally used, as well known in the art of extraction of aromatics with solvents.

DESCRIPTION OF THE DRAWING

The invention will be further described with reference to the drawings, in which FIG. 1 is a schematic diagram of the process according to the invention and FIG. 2 is a graph showing the effect of the process according to the invention on the pH of the water in the process system.

In FIG. 1, 10 is the extraction zone, to which feed material containing a mixture of aromatic and nonaromatic hydrocarbons is introduced through line 12. Solvent is introduced through line 14. Fresh solvent is introduced through line 13; recycled solvent, through line 15. Suitable conventional means are employed for intimate contacting of solvent with feed material in zone 10. Raffinate containing nonaromatic components is withdrawn through line 16 and solvent containing extracted aromatic components and some nonaromatic components is removed through line 18 and introduced into solvent stripping zone 20, in which nonaromatic components are stripped with water introduced through line 21 and distilled overhead through line 22 and recycled to extraction zone 10. Aromatic components are distilled in zone 20 and removed through line 24 to water washing zone 26. The solvent residue from stripping zone 20 is recycled through line 15 to extraction zone 10. The raffinate from zone 10 is passed through line 16 into water washing zone 28. Water is introduced through line 30 into washing zone 26 and is contacted therein with the aromatic extract to remove residual solvent therefrom. The water-washed aromatic extract is removed through line 32 for further conventional processing. Wash water passes through line 34 into washing zone 28 and is contacted therein with the raffinate to remove residual solvent therefrom. The water-washed raffinate is removed through line 36 for further conventional processing. Water containing solvent washed from the extract and raffinate is passed through lines 38, 40 and 42 to filter zone 44, wherein it is filtered by conventional means to remove particulate matter therefrom, and then is passed through line 46 to resin treatment zone 48 wherein it is contacted with ion exchange resin to remove acidic contaminants. The treated water passes through lines 50 and 21 into stripping zone 20. A portion of the water in line 38 is recycled through lines 52 and 30 into washing zone 26. Makeup water is added as needed through line 54.

Since it is not necessary to treat all of the water effluent from zone 28 in order to obtain the benefits of the invention, a bypass line 56 is provided in this embodiment. In typical operation, all of the water in line 38 is passed through line 56 until the pH of the water drops to, say, 6.8, whereupon part of the water in line 38 is passed through line 42 to filter and resin zones 44 and 48 until the pH rises to, say, 7.3, at which time the flow through line 42 is stopped and flow of all the water through line 56 is resumed.

The following example illustrates the invention:

Although the treatment with resin is shown in FIG. 1 as being applied to the process water directly after removal from the water washing operations, it is to be understood that such treatment may alternatively be applied to the process water at any other point in the circulation system therefor.

An operation substantially as illustrated in FIG. 1 was carried out on a feed stock comprising motor reformate, using tetraethylene glycol (TEG) as solvent. The passage of water through the filter and the resin bed was begun on a day hereinafter identified as 1 and operation continued thereafter, either passing one half of the water effluent from the washing zone (28 in FIG. 1) through the filter and resin bed, or bypassing all of the water from zone 28 around the filter and resin bed, as indicated by line 54 in FIG. 1. Two resin beds were used, one functioning as backup while the other was being used or regenerated. Flow of water was through only one of the resin beds at a time. Each of the resin beds contained about ten cubic feet of resin.

In FIG. 2, the pH of the water collected from the washing zones is shown as a function of time. Flow of water through the resin bed took place in the periods between each arrow-up sign and the next arrow-down sign, and was discontinued for the periods between each arrow-down sign and the next arrow-up sign. The results show the effectiveness of the treatment according to the invention to maintain the pH at a desired level. Without the treatment according to the invention, the pH falls to and remains at undesirably low levels, with resulting corrosion problems.

In Table I, the pH of the water collected from the washing zones, as well as the total dissolved solids (TDS) concentration and the concentrations of various metal ions therein, are shown at various times. In Table I, Runs 1, 2, 3, 4, 5, 6, 7, 8 and 9 were conducted 93, 86, 79, 72, 65, 58, 44, 37 and 6 days respectively prior to the beginning of the process according to the invention as described above, and Runs 10, 11, 12, 13, 14 and 15 were conducted 5, 27, 35, 39, 46 and 54 days, respectively after said beginning.

TABLE I

| Run | TDS ppm | Cu ppm | Ni ppm | Fe ppm | Na ppm |
|---|---|---|---|---|---|
| 1 | 5.5 | 0.00 | 0.00 | 9.54 | — |
| 2 | 5.9 | 0.01 | 0.00 | 6.54 | — |
| 3 | 6.3 | 0.01 | 0.00 | 7.53 | — |
| 4 | 5.9 | 0.04 | 0.22 | 6.72 | — |
| 5 | 5.6 | 0.03 | 0.01 | 6.85 | — |
| 6 | 5.9 | 0.00 | 0.00 | 4.78 | — |
| 7 | 6.3 | 0.00 | 0.00 | 4.15 | — |
| 8 | 6.2 | 0.02 | 0.01 | 4.33 | — |
| 9 | 6.3 | 0.01 | 0.00 | 2.30 | — |
| 10 | 6.8 | 0.00 | 0.00 | 1.99 | 1.33 |
| 11 | 8.0 | — | — | 0.66 | — |
| 12 | 8.8 | — | — | 0.83 | 2.86 |
| 13 | 8.2 | 0.00 | 0.03 | 0.10 | 5.71 |
| 14 | 8.1 | 0.02 | 0.01 | 0.17 | 7.54 |
| 15 | 8.8 | 0.02 | 0.00 | 0.14 | 6.95 |

Acceptable concentration of TDS is up to 250 ppm and of sodium ion, apparently as a consequence of regenerating the resin bed with sodium hydroxide, is up to 50 ppm.

The results in Table I show that the process of the invention resulted in a highly desirable lowering of the iron concentration, indicating substantial reduction in corrosion.

The following Table II shows corrosion data in mils per year (MPY) obtained by exposing stainless steel coupons to the corrosive medium for about a month, measuring the change in thickness and calculating the loss of metal in MPY. Data are given for eight periods prior to the period in which the process according to the invention was carried out, as compared with the period from the 13th to 25th days after the beginning of the process of the invention. In Table II, Locations A, B, C and D are heat exchangers respectively for the solvent and extract feed to the stripping zone (A), for the stripper overhead (B) and for the aromatics removed from the stripping zone (C and D).

TABLE II

| | Corrosion - MPY | | | | | | | | |
|---|---|---|---|---|---|---|---|---|---|
| | Prior Periods | | | | | | | | Days |
| Location | 1 | 2 | 3 | 4 | 5 | 6 | 7 | 8 | 13-25 |
| A-shell side outlet | 4.3 (8.2 pH) | 8.4 (7.0 pH) | 17 (5.6 pH) | 29 (6.1 pH) | 6.3 — | — — | — (5.6 pH) | 5.7 (5.9 pH) | 2.9 (7.8 pH) |
| B-outlet | 0.2 (8.5 pH) | 1.4 (7.0 pH) | 3.9 (5.7 pH) | 3.2 (5.7 pH) | 1.5 — | — — | — — | — — | — (8.0 pH) |
| C-return header | 2.5 (7.0 pH) | 11.6 (6.3 pH) | 21 (5.8 pH) | 16 (5.6 pH) | 3.0 (7.0 pH) | 11.5 — | 14.2 (5.3 pH) | — (5.4 pH) | — (7.1 pH) |
| D-return header | — (8.5 pH) | — (7.0 pH) | — (5.7 pH) | — (5.7 pH) | 2.4 (8.3 pH) | — — | — (5.5 pH) | 28 (5.9 pH) | 1.4 (8.0 pH) |

The relatively high pH and low corrosion rates in Period I are apparently the result of neutralization of acidity by a treatment with amine conducted during that period. The results for Days 13–25 show the beneficial effect of the process according to the invention.

The invention claimed is:

1. In a process wherein aromatics are extracted from nonaromatics by a selective solvent, extracted aromatics are separated from the bulk of the solvent and washed with water in a washing zone to remove residual solvent, and said water is withdrawn from said washing zone, the improvement which comprises reducing corrosion in the system by contacting said water after said withdrawal with an anion exchange resin to remove acidic components.

2. Process according to claim 1 wherein said ion exchange resin contains tertiary amine functional groups or quaternary ammonium functional groups.

3. Process according to claim 1 wherin said solvent is a polyalkylene glycol.

4. Process according to claim 3 wherein said solvent is tetraethylene glycol.

* * * * *